United States Patent [19]

Kosal et al.

[11] Patent Number: 5,045,360

[45] Date of Patent: Sep. 3, 1991

[54] SILICONE PRIMER COMPOSITIONS

[75] Inventors: Jeffrey A. Kosal, Midland; Terence J. Swihart, Essexville, both of Mich.

[73] Assignee: Dow Corning Corporation, Midland, Mich.

[21] Appl. No.: 648,757

[22] Filed: Jan. 31, 1991

Related U.S. Application Data

[62] Division of Ser. No. 426,835, Oct. 26, 1989, Pat. No. 5,008,349.

[51] Int. Cl.$^5$ ............................................. B05D 3/02
[52] U.S. Cl. ................................... 427/387; 427/387.1; 427/54.1; 427/44; 525/477
[58] Field of Search ............. 525/477; 427/387, 389.1, 427/54.1, 44

[56] References Cited

U.S. PATENT DOCUMENTS

| Re. 32,250 | 9/1986 | Plueddemann | 252/389.1 |
|---|---|---|---|
| 4,122,127 | 10/1978 | Mikami et al. | 260/825 |
| 4,267,297 | 5/1981 | Hanada et al. | 528/18 |
| 4,283,513 | 8/1981 | Mikami | 525/476 |
| 4,287,326 | 9/1981 | Mikami | 525/476 |
| 4,315,970 | 8/1982 | McGee | 428/412 |
| 4,343,856 | 8/1982 | Uram | 428/336 |
| 4,385,158 | 5/1983 | Mikami et al. | 525/476 |

FOREIGN PATENT DOCUMENTS 1350378  5/1978  Japan .

*Primary Examiner*—Melvyn I. Marquis
*Attorney, Agent, or Firm*—Alexander Weitz

[57] ABSTRACT

Silicone primer compositions comprising the reaction product of a resinous copolymeric siloxane and an organosilane are disclosed. The compositions find particular utility in promoting the adhesion of curable silicone coating compositions, comprising a liquid copolymeric organopolysiloxane and a polydiorganosiloxane, to solid substrates. Priming metal substrates with the certain compositions of the present invention additionally imparts improved corrosion resistance thereto when the substrates are subsequently coated with the above mentioned silicone coating compositions.

7 Claims, No Drawings

SILICONE PRIMER COMPOSITIONS

This is a divisional of copending application Ser. No. 07/426,835 filed on 10-26-89, now U.S. Pat. No. 5,008,349.

The present invention relates to silicone primer compositions. More particularly, the invention relates to primers comprising reaction products of a resinous copolymeric siloxane and certain organosilanes.

BACKGROUND OF THE INVENTION

It is well known in the coatings art that significant improvement in adhesion of a film to a substrate can be obtained by incorporating various adhesion promoters into the coating compositions or by employing such adhesion promoters as primers before coating the substrate. In this regard, the use of a wide-range of organosilicon compounds and compositions has greatly benefited the art.

Organosilicon compounds which are useful in these applications generally contain hydrolyzable groups (e.g., halogen, alkoxy) attached to the silicon atom thereof which generate silanol groups upon contact with ambient moisture, and thus readily form chemical and/or physical bonds with mineral and metal surfaces. Also attached to the silicon of the organosilane adhesion promoter is an organic moiety which is reactive with, or at least shows some affinity towards, one of the components of the coating (e.g., a film-forming polymer). In this way, a chemical or physical "molecular bridge" is believed to be formed between the coating and the substrate which results in the observed macroscopic improvement in adhesion. Due to the complex interactions among the substrate, primer and coating composition, however, this broadly stated description has only limited predictive value with respect to any specific system. Several examples of such adhesion-enhancing agents follow.

In U.S. Pat. No. 4,122,127, Mikami et al. disclose adhesion promoters for adhering silicone rubber to substrates. These adhesion promoter consist of an organopolysiloxane resin and an organopolysiloxane copolymer having at least one epoxy group and at least one unsaturated group attached thereto.

In U.S. Pat. No. 4,315,970, McGee describes a method of forming an adherent metal surface on a substrate by treating the substrate with at least one alkoxysilane, or a partial hydrolyzate thereof, having various reactive groups attached thereto. Adhesion of the metal to the substrate is enhanced by the use of the silane.

In U.S. Pat. No. 4,267,297, Hanada et al. teach room temperature curable silicone resins. These materials comprise (A) a hydroxylated organopolysiloxane, (B) an alkoxylated organopolysiloxane, (C) an alkoxysilane and (D) an aminoalkylalkoxysilane. Coatings formed from these resins are said to have excellent heat resistant, water repellency, mold release, weather resistance and storage stability.

Mikami, in U.S. Pat. Nos. 4,283,513 and 4,287,326, teaches resin compositions consisting essentially of a siloxane-modified epoxy resin, an alkoxy functional organopolysiloxane and a curing agent, such as carboxylic acid anhydrides. The compositions are said to have improved retention of electrical properties when exposed to moisture.

Mikami, in Japanese Patent Publication, O.P.I. number 13503/78, published May 10, 1978, further teaches a silicone resin composition comprising an organopolysiloxane resin, an alkoxysilane having alkyl or alkenyl groups attached thereto, an aminoalkylalkoxysilane and an organic solvent.

In U.S. Pat. No. 4,385,158 to Mikami et al., there is disclosed a room temperature curable, one component epoxy resin modified silicone resin having heat resistance and adhesion to substrates. The silicone resin component of this composition consists of an organopolysiloxane resin, a monovalent organo-substituted alkoxysilane and an aminoalkylalkoxysilane adhesion promoter.

In U.S. Pat. No. 4,343,857 to Uram, there is disclosed a coating for optical members comprising a prehydrolyzed alkyl silicate, a polysilicic acid and a monocarboxylic acid dispersed in an aqueous vinyl interpolymer and an epoxy binder containing a filler of fumed silica or aluminum oxide and a silane. The compositions are said to result in hard coatings for optical systems which are stable with respect to hydrolysis.

Plueddemann, in U.S. Pat. No. Re. 32,250, teaches that salts of certain nitrogen or sulfur containing siliconate compositions are useful as stabilizers for aqueous silicates in such applications as treating boiler water, geothermal water and in antifreeze solutions. This patent discusses the precursors of said salts and the preparation thereof from, e.g., the reaction of an aminosilane with either an acrylic acid or ester.

Although the above cited art discloses various silanes in combination with a variety of organofunctional silicone resins, it does not suggest the primer compositions of the present invention which are based on the reaction product of a resinous copolymeric siloxane with certain organofunctional silanes, as described infra.

SUMMARY OF THE INVENTION

The present invention, therefore, relates to silicone primer compositions comprising the reaction product of:

(A) a resinous copolymeric siloxane consisting essentially of $R_3SiO_{\frac{1}{2}}$ units and $SiO_{4/2}$ units wherein the ratio of $R_3SiO_{\frac{1}{2}}$ units to $SiO_{4/2}$ units is 0.4:1 to 1.2:1 and each R independently denotes a monovalent hydrocarbon radical, said siloxane resin having residual hydroxyl functionality thereon; and (B) a silane selected from the group consisting of those having the formulas

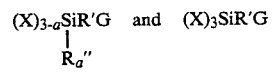

wherein X is selected from the group consisting of an alkoxy group having 1 to 3 carbon atoms, an acyloxy group having 2 to 4 carbon atoms and a halide radical, R' is a divalent hydrocarbon group having 2 to 8 carbon atoms, R" is selected from the group consisting of an alkyl radical having 1 to 12 carbon atoms and a phenyl radical, a is 1 or 2 and G is selected from the group consisting of (i) an acryl group selected from the group consisting of

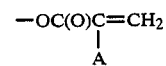

and

-continued $$-\text{NC(O)C}=\text{CH}_2$$
$$\phantom{-NC(O)}\mid\phantom{C=}\mid$$
$$\phantom{-NC(O)}A\phantom{C=}A$$

in which A is independently selected from the group consisting of hydrogen and a methyl radical,
(ii) a glycidoxy group,
(iii) an aromatic group of the formula

[benzene ring]—CH₂Cl (iv) an analino group and
(v) an amine group selected from the group consisting of —NHQ and —NQ₂
wherein Q is independently selected from the group consisting of

—CH₂COOR'''

—CH₂CH₂COOR'''

—CHCOOR'''
  |
  CH₂COOR'''

—CH₂CHCOOR'''
  |
  CH₂COOR''' and

—CH₂CH₂N(CH₂CH₂COOR''')₂ in which R''' is an alkyl radical having 1 to 3 carbon atoms, the ratio of said silane (B) to said siloxane resin (A) being such as to provide from about 0.1 to about 3 equivalents of X for each equivalent of hydroxyl of said component (A).

DETAILED DESCRIPTION OF THE INVENTION

Component (A) of the present invention is a resinous copolymeric siloxane which consists essentially of $R_3SiO_{1/2}$ siloxane units and $SiO_{4/2}$ siloxane units in a molar ratio which provides from 0.4 to 1.2 $R_3SiO_{1/2}$ unit for every $SiO_{4/2}$ unit. Each R denotes a monovalent hydrocarbon radical; such as an alkyl radical, such as methyl, ethyl, isopropyl, butyl and hexyl; an alkenyl radical, such as vinyl and allyl; an aryl radical, such as phenyl, tolyl and xylyl; an arylalkyl radical, such as beta-phenylethyl and beta-phenylpropyl; and a cycloaliphatic radical, such as cyclopentyl, and cyclohexyl. Preferably all R radicals in ingredient (a) are lower alkyl radicals although a minor portion of them can be replaced with other monovalent hydrocarbon radicals such as the vinyl radical and/or the phenyl radical to provide additional properties for the resinous copolymer such as the reactivity attendant therewith. The resinous copolymeric siloxane further contains reactive hydroxyl groups attached to the silicon atoms thereof. Generally, the resinous copolymeric siloxane contains about 0.5 to 5 weight percent, on a solids basis, of such hydroxyl groups.

It is preferred that the resinous copolymeric siloxane (A) consists essentially of $(CH_3)_3SiO_{1/2}$ siloxane units and $SiO_{4/2}$ siloxane units, in the molar ratio of about 0.75:1, wherein the hydroxyl content is about 2.5 to 3.8 weight percent on a solids basis.

Resinous copolymeric siloxanes are well known in the art and are typically prepared in an organic solvent which can also conveniently serve as the reaction medium during the reaction with component (B), described infra. The particular organic solvent employed is not critical; it can be, for example, an aliphatic hydrocarbon, an aromatic hydrocarbon or halogenated derivatives thereof, or mixtures of such solvents. Particularly useful organic solvents include benzene, toluene, xylene, trichloroethylene and mineral spirits.

The above described resinous copolymeric siloxane (A) is reacted with an organofunctional silane (B) having one of the following general formulas $$(X)_{3-a}SiR'G \text{ or } (X)_3SiR'G$$
$$\phantom{(X)_{3-a}Si}\mid$$
$$\phantom{(X)_{3-a}Si}R''_a$$

to form the compositions of the present invention. In the formulas for component (B), X is selected from the group consisting of an alkoxy group having 1 to 3 carbon atoms, an acyloxy group having 2 to 4 carbon atoms and a halide radical, R' is a divalent hydrocarbon group having 2 to 8 carbon atoms, such as ethylene, propylene or isobutylene, R'' is selected from the group consisting of an alkyl radical having 1 to 12 carbon atoms and a phenyl radical, a is 1 or 2 and G is a monovalent organic moiety, described infra. Preferably, component (B) has the structure $(X)_3SiR'G$, wherein X is an alkoxy group, most preferably a methoxy group.

The group G of component (B) may be selected from the group consisting of
(i) an acryl group selected from the group consisting of an acryloxy group of the formula $$-\text{OC(O)C}=\text{CH}_2$$
$$\phantom{-OC(O)}\mid$$
$$\phantom{-OC(O)}A$$

and an acrylamide group of the formula $$-\text{NC(O)C}=\text{CH}_2$$
$$\phantom{-NC(O)}\mid\phantom{C=}\mid$$
$$\phantom{-NC(O)}A\phantom{C=}A$$

in which A is independently selected from the group consisting of hydrogen and a methyl radical,
(ii) a glycidoxy group of the formula

—O—CH₂CH——CH₂
         \  /
          O (iii) an aromatic group of the formula

[benzene ring]—CH₂Cl and
(iv) an analino group of the formula

—N—Ph
 |
 H wherein Ph hereinafter denotes a phenyl radical.

Specific examples of the foregoing organosilanes include gamma-methacryloxypropyltrimethoxysilane, gamma-glycidoxypropyltrimethoxysilane, and the structures (MeO)₃Si—C₆H₄—CH₂Cl (ORTHO, META, PARA)

(MeO)₃Si—CH₂CH₂CH₂—N—Ph
                    |
                    H (MeO)₂Si—CH₂CH₂CH₂—OC(O)CH=CH₂
    |
    Me (MeO)Si—CH₂CH₂CH₂—OC(O)CH=CH₂
   |
   Me₂

(AcO)₃Si—CH₂CH₂CH₂—N—Ph
                   |
                   H (EtO)₃Si—CH₂CH₂CH₂—C₆H₄—CH₂Cl (MeO)₃Si—CH₂CH₂CH₂—NC(O)CH=CH₂
                   |
                   H (MeO)₃Si—CH₂CH₂CH₂—NC(O)C=CH₂
                   |    |
                   H    Me (MeO)₃Si—CH₂CH₂CH₂—NC(O)CH=CH₂ and
                   |
                   Me (MeO)₃Si—CH₂CH₂CH₂—NC(O)C=CH₂
                   |   |
                   Me  Me wherein Me, Ac and Et hereinafter denote methyl, acetyl and ethyl radicals, respectively.

Alternatively, G of the organofunctional silane (B) may also be (v) an amine selected from the group consisting of the general formulas

—NHQ and

—NQ₂ wherein Q is independently selected from the group consisting of

—CH₂COOR‴

—CH₂CH₂COOR‴

—CHCOOR‴
 |
 CH₂COOR‴

—CH₂CHCOOR‴
     |
     CH₂COOR‴ and

-continued
—CH₂CH₂N(CH₂CH₂COOR‴)₂ in which R‴ is an alkyl radical having 1 to 3 carbon atoms. Preferably, the group Q is selected from the groups —CH₂CH₂COOMe and —CH₂CH₂N(CH₂CH₂COOMe)₂

A highly preferred organosilane (B) of this type is the structure (L)₂N—CH₂CH₂NCH₂CH₂CH₂Si(OMe)₃
            |
            L in which L is the group —CH₂CH₂COOMe.

All the above compounds from which component (B) may be selected are well known in the art and further description thereof is considered unnecessary.

The compositions of the present invention may be prepared by reacting resinous copolymeric siloxane (A) with organosilane (B) in such a ratio as to provide from about 0.1 to about 3 equivalents of X for each equivalent of hydroxyl group present in component (A). The aforementioned ratios have generally been found to result in clear primer compositions. In this regard, a highly preferred embodiment of the present invention is obtained when organosilane (B) has the preferred structure (MeO)₃SiR'G and the molar ratio of methoxy groups to hydroxyl is about 3:1.

For the purposes of the present invention, the hydroxyl content of the resinous copolymeric siloxane (A) may readily be determined by $Si^{29}$ nmr (nuclear magnetic resonance). In accordance with this well known method, a silicon-free background is used (e.g., a non-glass probe) to achieve accurate quantitative results.

The reaction of components (A) and (B) is carried out in an organic solvent such as those employed in the preparation of component (A), above. Preferably, this is accomplished at about 10 to 80 weight percent solids. The reaction may proceed at room temperature (e.g., for about 0.5 to 48 hours) or at elevated temperatures up to about 150° C. (e.g., for about 5 to 180 minutes). Generally, the completion of the reaction may be determined by the cessation of the generation of HX as the X group of the organosilane (B) reacts with the hydroxyl of the resinous copolymeric siloxane (A). Thus, for example, when X is the preferred methoxy group, reaction is essentially complete when the methanol generated has reached its maximum. The skilled artisan can thus readily assess the extent of reaction by routine analytical methods such as gas chromatography. In the above example, wherein methanol is the reaction by-product, simply distilling the methanol overhead as the reaction mixture is heated provides an adaquate indication of completion. It should be noted, however, that one should not expect an exact stoichiometric correspondence between the amount of HX formed and the amount of hydroxyl present in the resinous copolymeric siloxane (A) since some of the hydroxyl groups which are detectable by $Si^{29}$ nmr are hindered and therefore not reactive under the above conditions.

When the Group G of the organofunctional silane (B) is the above described amine (v) of the general formula —NHQ or —NQ$_2$, it is further contemplated that water-dispersible compositions of the present invention may be prepared by soponifying residual carboxylate functionality (i.e., —COOR''' groups) of the reaction product of (A) and (B) with an aqueous alkali solution (e.g., NaOH or KOH). Such a procedure for forming the alkali salts of these carboxylates has been described in U.S. Pat. No. Re. 32,250, cited supra, and hereby incorporated by reference.

The primer compositions of the present invention may further contain catalysts, such as organotitanates and tertiary amines, fibers, fillers, flow agents, stabilizers, colorants and biocides, inter alia.

The compositions of the present invention may be applied from solution to prime solid substrates, such as metals, minerals, glass, rubbers, plastics, wood and concrete for the purpose of enhancing the adhesion of coatings thereto. Any of the commonly practiced coating or priming methods known in the art may be used to prime the substrate (e.g., spraying, knife coating, dipping, gravure application, roller application, curtain coat and electrodeposition techniques). Typically, such prime coats are considerably thinner than the subsequent top coat, usually in the range of 0.05 to 1 mil in thickness, and thus require low application viscosities. To this end, the viscosity of the primer compositions may be adjusted downward by the further addition of organic solvents, such as those discussed above.

When the compositions of the present invention contain acryl groups (e.g., when G of silane (B) is an acryloxy or acrylamide group), they may be further cured on substrates by exposure to ultraviolet light or an electron beam, according to well known methods in the art.

The primer compositions of the present invention are particularly useful in conjunction with curable silicone coating compositions comprising a liquid copolymeric organopolysiloxane and a polydiorganosiloxane. These coating compositions have been described in U.S. Pat. Nos. 4,322,518 to Blizzard, 4,537,829 to Blizzard and Swihart, and 4,701,380 to Narula et al. The three aforementioned patents are assigned to the assignee of the present invention and the full disclosure of each is hereby incorporated by reference. It has been found that, when such compositions are coated and cured over the primers of the present invention, improved corrosion resistance is imparted to a metal substrate versus the coatings wherein the primer is not used.

Other utilities contemplated for the primer compositions include: surface modification agents for human skin and hair; conditioning additives for shampoos; treatments for surface modification of textiles and paper fibers; crosslinkers and physical property modifiers in silicone and organic resins, plastics and rubbers; and modifiers of silicone and organic adhesives. Additionally, the abovementioned saponified compositions of this invention may be used as lubricants in grease compositions.

EXAMPLES

The following examples are presented to further illustrate the compositions and methods of this invention, but are not to be construed as limiting the invention, which is delineated in the appended claims. All parts and percentages in the examples are on a weight basis unless indicated to the contrary.

The following materials were employed in the following examples to illustrate the compositions of the present invention as well as comparative compositions:

RESIN 1 is a 65% xylene solution of a siloxane resin copolymer consisting essentially of (CH$_3$)$_3$SiO$_{1/2}$ units and SiO$_2$ units in a molar ratio of approximately 0.75:1. This resin had an approximate hydroxyl group content of about 3% as determined by Si$^{29}$ nmr (on a solids basis), which corresponds to about 0.1 mole of hydroxyl groups per 100 grams of the resin solution.

SILANE A is a silane consisting essentially of

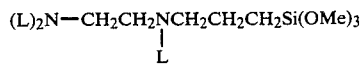

wherein L is the group -CH$_2$CH$_2$COOMe and Me hereinafter denotes a methyl radical. This material was prepared by slowly adding 28 parts of methylacrylate to a mixture of 23 parts of a silane consisting essentially of N-(beta-aminoethyl)-gamma-aminopropyltrimethoxysilane and 49 parts of methanol and reacting the resulting composition at about 67° C. for 2 hours.

SILANE B is a silane consisting essentially of gamma-glycidoxypropyltrimethoxysilane.

SILANE C is a silane consisting essentially of gamma-methacryloxypropyltrimethoxysilane.

SILANE D is a silane consisting essentially of

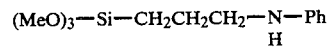

wherein Ph hereinafter denotes a phenyl radical.

SILANE E is a silane consisting essentially of

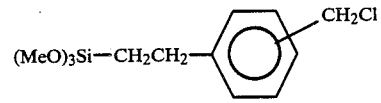

(a mixture of meta- and para- isomers obtained from Petrarch Systems, Bristol, Pa.).

SILANE F is a phosphate ester silane consisting essentially of

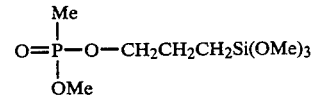

SILANE G is a silane consisting essentially of gamma-aminopropyltriethoxysilane.

SILANE H is a silane consisting essentially of methyltrimethoxysilane.

SILANE I is a 42 weight percent solution of a silane consisting essentially of 3-(trimethoxysilyl)-propyloctadecyldimethyl ammonium chloride in methanol (i.e., n—C$_{18}$H$_{37+}$N(CH$_3$)$_2$—CH$_2$CH$_2$CH$_2$—Si(OMe)$_3$.Cl$^-$ in methanol).

SILANE J is a silane consisting essentially of

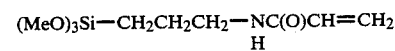

SILANE K is a silane consisting essentially of

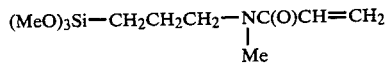

EXAMPLES 1-15

Ten gram portions of RESIN 1 were mixed with the quantities of SILANE A and SILANE F indicated in Table 1 and allowed to react at room temperature for about 16 hours. These solutions were then flow coated onto glass slides and the coated slides were either allowed to dry at room temperature or were heated at 80° C. for one hour. Final films were up to 5 mils thick. In addition, a control composition consisting of only RESIN 1 (Comparative Example 1) was evaluated, as shown in the last two columns of Table 1. The term "crazed" herein indicates that the film had surface and/or interior cracks detracted from its clarity, appearance and integrity.

TABLE 1

| Coating Composition | Grams SILANE A | Grams SILANE F | Film Properties Dried at Room Temperature | Heated at 80° C. for 1 hour |
| --- | --- | --- | --- | --- |
| (Comparative) Example 1 | 0 | 0 | crazed, powder film | powder consistency |
| (Comparative) Example 2 | 0.5 | 0 | " | " |
| (Comparative) Example 3 | 0.75 | 0 | " | — |
| Example 4 | 1.0 | 0 | crazed but difficult to remove film | — |
| Example 5 | 1.5 | 0 | clear film | — |
| Example 6 | 2.0 | 0 | " | clear, tough film |
| Example 7 | 2.5 | 0 | clear, somewhat soft film | — |
| Example 8 | 3.0 | 0 | " | — |
| Example 9 | 3.5 | 0 | very slightly hazy, somewhat soft film | — |
| Example 10 | 4.0 | 0 | slightly hazy, soft film | — |
| Example 11 | 4.5 | 0 | hazy, soft wax film (m.p. 130-140° C.) | — |
| Example 12 | 5.0 | 0 | " | — |
| (Comparative) Example 13 | 0 | 0.5 | crazed, powder film | hazy, brittle powder |
| (Comparative) Example 14 | 0 | 2.0 | hazy, slightly brittle film | hazy, brittle film |
| (Comparative) Example 15 | 0 | 5.0 | " | " |

EXAMPLES 16-25

Mixtures of RESIN 1 and the silanes shown in Table 2 were made in the indicated ratios based on the hydroxyl content of the resin. These mixtures were allowed to react at room temperature for four hours, whereupon coatings on glass slides were prepared, as described above. After drying for about 4 hours at room temperature, the coatings were examined for clarity, dryness, tack and flexibility. These observations are also reported in Table 2.

TABLE 2

| Silane Additive | Molar Ratio of Methoxy Functionality of Silane to Hydroxyl Functionality of Resin 1 | | |
| --- | --- | --- | --- |
| | 1.5 | 3.0 | 6.0 |
| Example | | | |
| 16 SILANE A | clear, flexible film | clear, soft film | sl. hazy/waxy film |
| 17 SILANE B | clear, soft film | clear, very tacky | clear, not dry |
| 18 SILANE C | clear, soft film | clear, very tacky | clear, not dry |
| 19 SILANE D | clear, firm film | clear, very tacky | hazy, tacky |
| 20 SILANE E | — | clear, very tacky | — |
| (Comparative) Example | | | |
| 21 SILANE F | clear, brittle film | sl. haze/crazed | hazy/crazed |
| 22 SILANE G | crazed | crazed | crazed |
| 23 SILANE H | completely crazed | completely crazed | completely crazed |
| 24 SILANE I | — | hazy, waxy material | — |
| 25 NONE (CONTROL) | samples completely crazed | | |

EXAMPLE 26

Five grams of RESIN 1 was weighed into a ½ oz. vial and one gram of SILANE J was added and mixed therewith. The resulting mixture was slightly hazy. A glass slide was coated with the mixture and allowed to air dry for 2 hours at room temperature. Although the coating was relatively thick, it dried under these conditions to produce a slightly hazy, non-crazed, brittle film.

In a separate experiment, one drop of the above mixture of RESIN 1 and SILANE J was spread out on a glass slide so as to cover the entire surface of the slide. While still wet, the slide was irradiated under an electron beam (dose=5 megarads; exposed under a nitrogen atmosphere containing 300 parts per million oxygen). The resulting radiation-cured film was clear, non-sticky and very tough.

EXAMPLE 27

The procedures of Example 26 were repeated using SILANE K in place of SILANE J. The mixture of RESIN 1 with SILANE K was clear, as was the electron beam-cured coating prepared therefrom.

EXAMPLE 28

A mixture consisting of 2 grams of SILANE A and 10 grams of RESIN 1 was further diluted with xylene to provide a primer solution having a solids content of 5 percent. This primer solution was coated onto a clean aluminum panel and allowed to dry at room temperature.

A topcoat liquid silicone resin solution was prepared by mixing 17.7 grams of a 32% toluene solution of a silanol-ended dimethylpolysiloxane gum having a viscosity of about 200,000 Poise at 25° C., 2.3 grams of a liquid organopolysiloxane copolymer prepared according to Example 1 of U.S. Pat. No. 4,701,380, cited supra, and 380 grams of heptane solvent. This mixture was then catalyzed with 0.25 gram of dibutyltin diacetate.

The catalyzed topcoat composition was applied to the primed aluminum panel using a Gardner blade. The silicone topcoat was then heat cured at 150° C. for 15 minutes. An unprimed control panel coated with the silicone composition was similarly prepared for comparison. The coatings were scribed with an "X" pattern to expose bare aluminum metal and were then subjected to a salt spray test according to the protocol of ASTM Test Method B-117 at 95° F. using a 5% sodium chloride solution.

After 96 hours in the salt spray apparatus, the panel which was not first primed with the composition of the present invention showed extensive corrosion of the aluminum in the scribed area while the scribed area of the primed panel exhibited no corrosion and retained a bright appearance.

We claim:

1. In a method for improving the adhesion of a coating to a substrate by applying a primer between said substrate and said coating, the improvement comprising using as said primer the reaction product of:
   (A) a resinous copolymeric siloxane consisting essentially of $R_3SiO_{1/2}$ units and $SiO_{4/2}$ units wherein the ratio of $R_3SiO_{1/2}$ units to $SiO_{4/2}$ units is 0.4:1 to 1.2:1 and each R independently denotes a monovalent hydrocarbon radical, said siloxane resin having residual hydroxyl functionality thereon; and
   (B) an organosilane selected from the group consisting of those having the formulas

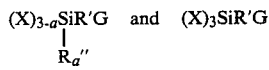

wherein X is selected from the group consisting of an alkoxy group having 1 to 3 carbon atoms, an acyloxy group having 2 to 4 carbon atoms and a halide radical, R' is a divalent hydrocarbon group having 2 to 8 carbon atoms, R" is selected from the group consisting of an alkyl radical having 1 to 12 carbon atoms and a phenyl radical, a is 1 or 2 and G is selected from the group consisting of
   (i) an acryl group selected from the group consisting of

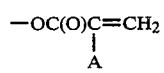

and

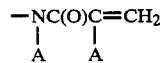

in which A is independently selected from the group consisting of hydrogen and a methyl radical,
   (ii) a glycidoxy group,
   (iii) an aromatic group of the formula

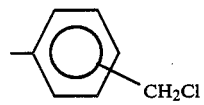

(iv) an anilino group and
   (v) an amine group selected from the group consisting of

—NHQ and

—NQ$_2$ wherein Q is independently selected from the group consisting of

—CH$_2$COOR''',

—CH$_2$CH$_2$COOR''',

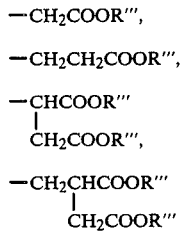

and

—CH$_2$CH$_2$N(CH$_2$CH$_2$COOR''')$_2$ in which R''' is an alkyl radical having 1 to 3 carbon atoms, the ratio of said silane (B) to said siloxane resin (A) being such as to provide from about 0.1 to about 3 equivalents of X for each equivalent of hydroxyl of said component (A).

2. The method according to claim 1, wherein group G of said organosilane (B) is

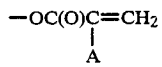

in which A is selected from the group consisting of hydrogen and a methyl radical.

3. The method according to claim 1, wherein group G of said organosilane (B) is

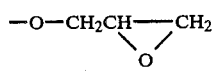

4. The method according to claim 1, wherein group G of said organosilane (B) is

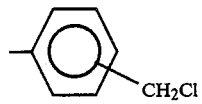

5. The method according to claim 1, wherein group G of said organosilane (B) is

—N—Ph
 H in which Ph denotes a phenyl radical.

6. The method according to claim 1, wherein group G of said organosilane (B) is selected from the group consisting of

—NHQ and

—NQ$_2$ in which Q is independently selected from the group consisting of

—CH₂COOR''',

—CH₂CH₂COOR''',

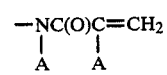

$$-\text{CH}_2\text{CHCOOR}''' \\ \quad\quad | \\ \quad\quad \text{CH}_2\text{COOR}'''$$

and

—CH₂CH₂N(CH₂CH₂COOR''')₂ in which R''' is an alkyl radical having 1 to 3 carbon atoms.

7. The method according to claim 1, wherein group G of said organosilane (B) is $$-\text{NC(O)C}=\text{CH}_2 \\ \; | \quad\quad | \\ \; A \quad\quad A$$

in which A is independently selected from the group consisting of hydrogen and a methyl radical.

* * * * *